United States Patent
Li et al.

(10) Patent No.: US 11,497,811 B2
(45) Date of Patent: Nov. 15, 2022

(54) WAFER AND CAPSULE FORMULATIONS WITH ENHANCED DISSOLUTION RATES FOR FENOFIBRATE

(71) Applicant: LTS Lohmann Therapie-Systeme AG, Andernach (DE)

(72) Inventors: Michael Li, West Caldwell, NJ (US); Markus Krumme, Allschwil (CH)

(73) Assignee: LTS Lohmann Therapie-Systeme AG, Anderdach (DE)

( * ) Notice: Subject to any disclaimer, the term of this patent is extended or adjusted under 35 U.S.C. 154(b) by 0 days.

(21) Appl. No.: 15/819,847

(22) Filed: Nov. 21, 2017

(65) Prior Publication Data

US 2018/0092979 A1 Apr. 5, 2018

Related U.S. Application Data

(62) Division of application No. 14/364,145, filed as application No. PCT/IB2012/000312 on Dec. 14, 2012, now Pat. No. 9,849,184.

(60) Provisional application No. 61/570,381, filed on Dec. 14, 2011.

(51) Int. Cl.

| | | |
|---|---|---|
| A61K 9/70 | (2006.01) | |
| A61K 31/216 | (2006.01) | |
| A61K 47/38 | (2006.01) | |
| A61K 9/16 | (2006.01) | |
| A61K 9/48 | (2006.01) | |
| A61K 47/10 | (2017.01) | |
| A61K 47/14 | (2017.01) | |

(52) U.S. Cl.
CPC ............ *A61K 47/38* (2013.01); *A61K 9/1688* (2013.01); *A61K 9/4833* (2013.01); *A61K 9/4858* (2013.01); *A61K 9/4866* (2013.01); *A61K 9/7007* (2013.01); *A61K 31/216* (2013.01); *A61K 47/10* (2013.01); *A61K 47/14* (2013.01)

(58) Field of Classification Search
None
See application file for complete search history.

(56) References Cited

U.S. PATENT DOCUMENTS

| | | |
|---|---|---|
| 5,785,976 A | 7/1998 | Westesen et al. |
| 8,524,280 B2 | 9/2013 | Fatmi et al. |
| 8,623,401 B2 | 1/2014 | Modi |
| 8,920,844 B2 | 12/2014 | Fatmi et al. |
| 2002/0047058 A1* | 4/2002 | Verhoff .................. A61K 9/14 241/26 |
| 2005/0096390 A1 | 5/2005 | Holm et al. |
| 2006/0210622 A1 | 9/2006 | Pace |
| 2006/0222706 A1 | 10/2006 | Flashner-Barak et al. |
| 2007/0014846 A1 | 1/2007 | Holm et al. |
| 2009/0246257 A1 | 10/2009 | Modi |
| 2009/0324710 A1 | 12/2009 | Glidden et al. |
| 2011/0052682 A1 | 3/2011 | Fatmi et al. |
| 2013/0323304 A1 | 12/2013 | Fatmi et al. |
| 2015/0182519 A1 | 7/2015 | Fatmi et al. |

FOREIGN PATENT DOCUMENTS

| | | |
|---|---|---|
| WO | WO 03/013501 | 2/2003 |
| WO | WO 2005/034920 | 4/2005 |
| WO | WO 2006/107316 | 10/2006 |
| WO | WO 2008/015959 | 7/2008 |
| WO | WO 2010/075065 | 7/2010 |

OTHER PUBLICATIONS

International Preliminary Report on Patentability issued in corresponding PCT Application No. PCT/IB2012/003123 dated Jun. 17, 2014.

* cited by examiner

*Primary Examiner* — Jessica Worsham
(74) *Attorney, Agent, or Firm* — Haug Partners LLP

(57) ABSTRACT

The invention relates to developing a novel water and capsule formulation using fenofibrate which is difficult to dissolve and control its release rate in vitro. For example, the invention relates to the creation of capsules and wafers comprising: fenofibrate, a surfactant, a carrier wax, a film former, a plasticizer, and optionally a super disintegrant or other ingredients. The invention further relates to the process of forming such capsules and wafers.

15 Claims, 9 Drawing Sheets

Figure 1 - Wafer dissolution rate for Example 2

Figure 2 - Wafer dissolution rate for Examples 3 and 4

CHITOSAN 6.3%
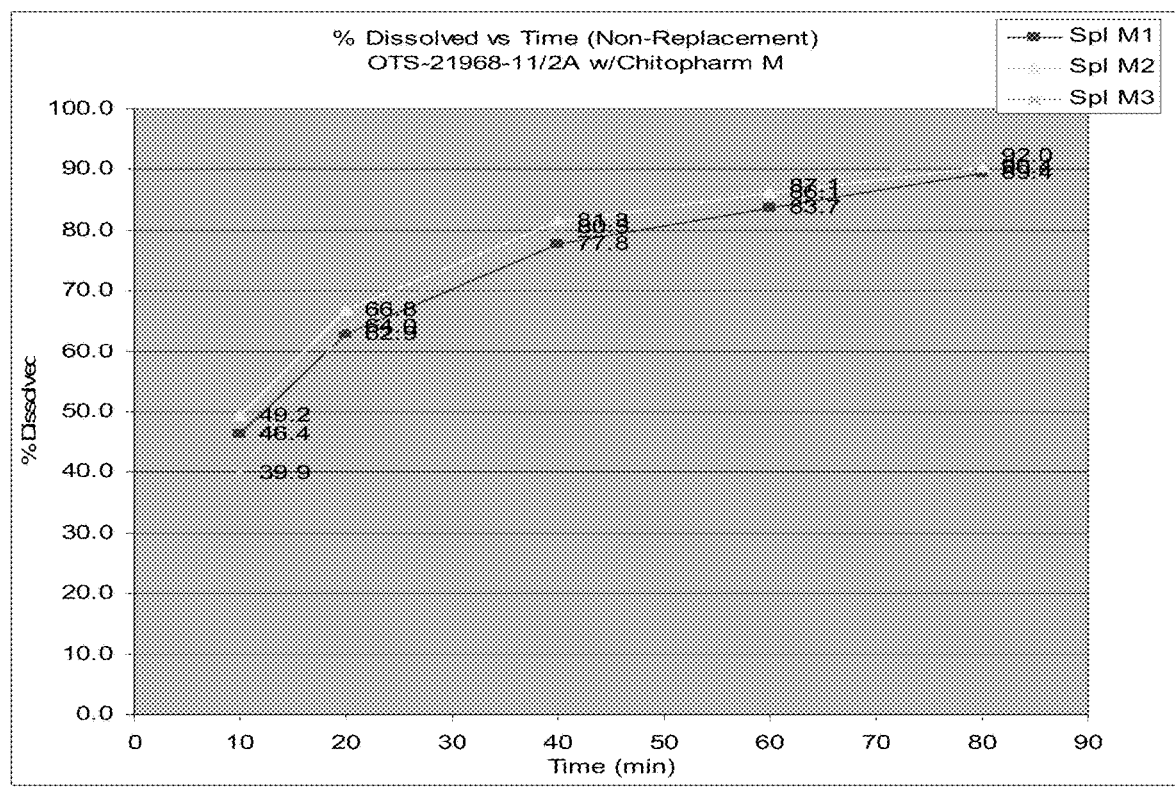
CHITOSAN 10.0 %
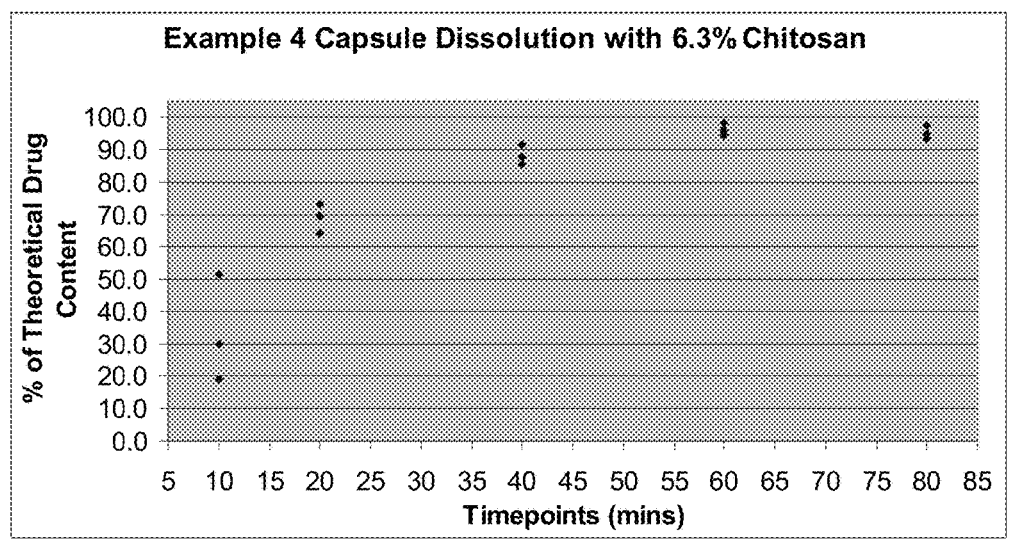
Figure 7

WAFER AND CAPSULE FORMULATIONS WITH ENHANCED DISSOLUTION RATES FOR FENOFIBRATE

INCORPORATION BY REFERENCE

The present application is a divisional of U.S. patent application Ser. No. 14/364,145 filed on Jun. 10, 2014, which claims priority from PCT Patent Application No. PCT/IB2012/003123 filed on Dec. 14, 2012, which claims priority from U.S. Provisional Patent Application No. 61/570,381 filed on Dec. 14, 2011, the disclosures of which are incorporated herein by reference in their entirety.

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

It is noted that citation or identification of any document in this application is not an admission that such document is available as prior art to the present invention.

The U.S. Food and Drug Administration's Biopharmaceutics Classification System (BCS) provides guidance for predicting the gastro-intestinal drug absorption. The drugs are classified in BCS based on the parameters of solubility and permeability. Cook et al., *AAPS J.*, 2008; 10(2): 206-310.

The BCS class boundaries are:

1. Solubility boundaries—It is based on the highest dose strength of an immediate release product. A drug is considered highly soluble when the highest dose strength is soluble in 250 mL or less of aqueous media over the pH range of 1 to 7.5. The volume estimate of 250 mL is derived from typical bioequivalence study protocols that prescribe administration of a drug product to fasting human volunteers with a glass of water.

Moreover, compounds can also be characterized by their dissolution rates wherein a rapidly dissolving compound is a compound where no less than 85% of the labeled amount of the drug substance dissolve within 30 minutes using USP Dissolution Apparatus 1 at 100 RPM or Apparatus 2 at 50 RPM in a volume of 900 ml or less in following media: 0.1 N HCl or simulated gastric fluid or pH 4.5 buffer and pH 6.8 buffer or simulated intestinal fluid.

2. Permeability boundaries—It is based indirectly on the extent of absorption of a drug substance in humans and directly on the measurement of rates of mass transfer across human intestinal membrane. Alternatively non-human systems capable of prediction the drug absorption systems capable of predicting the drug absorption in humans can be used (such as in-vitro culture methods). A drug substance is considered highly permeable when the extent of absorption in humans is determined to be 90% or more of the administered dose based on a mass-balance determination or in comparison to an intravenous dose.

BCS Class II compounds are drug substances with high permeability and low solubility. Examples of this category are glibenclamide/glyburide (antidiabetic), fenofibrate (an antilipemic), griseofulvin (antifungal) and lamotrigine (anticonvulsant). The bioavailability of these compounds is limited by their solubility (solvation rate). An in vitro and in vivo correlation can be found between the drug's solubility and its bioavailability.

Unfortunately, the in-vitro release rates of the class II active pharmaceutical compounds according to the BCS definition are such that these types of compounds are only very slightly water soluble which is problematic for delivering a drug for in vivo use by a patient in need of the pharmaceutical compound. Hence, the absorption of a poorly water-soluble compound from orally administered solid dosage form is controlled by its dissolution rate in the gastrointestinal fluid present at the absorption site.

One solution to the problem of low aqueous solubility of class II pharmaceuticals is the use of liquisolid systems to form tablets and capsules whereby a non-aqueous active drug solution or non-polar liquid active drug is combined with a suitable carrier material to form wet particles which are then combined with a coating material to form a liquisolid system. The liquisolid system is then further processed to form tablets and capsules. See for example, U.S. Pat. No. 6,096,337 and Yadav et al., "Enhancement of Solubility and Dissolution Rate of BCS Class II Pharmaceuticals by Nonaquious Granulation Technique", *Int. J. Pharma. Res. Dev.*, vol. 1, issue 12, pages 1-12, February 2008 (ISSN: 0974-9446).

However, the formation of liquisolid systems places special requirements on the components used such as simultaneously requiring good flow and good compression properties when forming the liquisolid system. In addition, any excipient used must possess large surface areas and fine particle sizes while not affecting the good flow and good compression achieved by the other components of the liquisolid system.

Another solution is the use of polyethylene oxide (PEO) in combination with griseofulvin to form the so called "solid solution". The solid solution is formed by mixing the active drug with PEOs and then granulated and subsequently compressed into tablets.

However, the formation of solid solution needs energy intensive mixing using AMF-type mixers and the particle size of the granulation cannot easily be controlled.

As such, there still exists a need in the art to produce a dosage form which allows for the administration of BCS Class II active compounds, such as fenofibrate, which are user friendly, easy to administer and also produce a desirable pharmaceutical effect despite their low solubility in aqueous media.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed product, process of making the product or method of using the product, which meets the written description and enablement requirements of the USPTO (35 U.S.C. 112, first paragraph) or the EPO (Article 83 of the EPC), such that applicant(s) reserve the right to disclaim, and hereby disclose a disclaimer of, any previously described product, method of making the product, or process of using the product.

SUMMARY OF THE INVENTION

The objective of this invention is to develop a novel wafer and capsule formulation using fenofibrate which is difficult to dissolve and control its release rate in vitro. Since an in vitro and in vivo correlation can be found for this class of compounds, therefore it is highly desirable to design a formulation with controllable in vitro release rate.

These and other embodiments are disclosed or are apparent from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 7 depicts the capsule formulation dissolution rate with super disintegrants

DETAILED DESCRIPTION OF EMBODIMENTS

Figure 1:
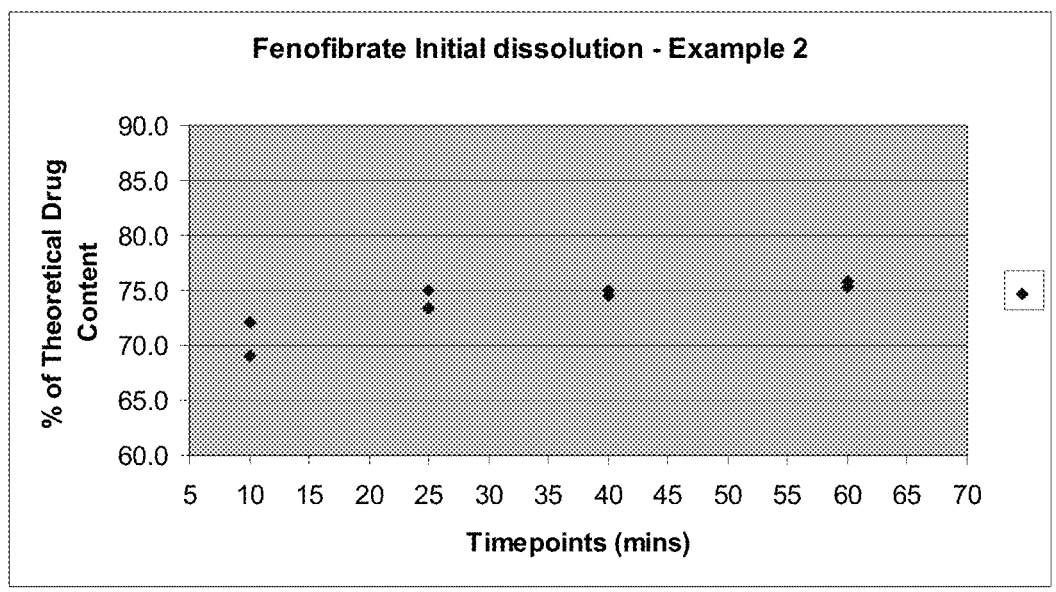
FIG. 1 depicts the wafer dissolution rate of Examples 1 and 2.

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

It has been found that wafer or capsule dosage forms can be formed which allow for the administration of Class II active compounds with a controlled release rate and/or enhanced dissolution which produces the desired pharmaceutical effect despite their low solubility in aqueous media.

For the purposes of this invention the term strips, thin film and wafers are considered to be interchangeable.

One aspect of the invention is a wafer which comprises of fenofibrate, surfactant, carrier wax, film former, plasticizer and optionally additional ingredients.

In one embodiment of the invention, the wafer comprises of:
 (a) 10 to 50% w/w of fenofibrate;
 (b) 10 to 50% w/w of surfactant;
 (c) 1 to 30% w/w of carrier wax;
 (d) 10 to 60% w/w of film former; and
 (e) 1 to 10% w/w of plasticizer.

In another embodiment of the invention, the wafer comprises of:
 (a) 20 to 40% w/w of fenofibrate;
 (b) 15 to 45% w/w of surfactant;
 (c) 2 to 20% w/w of carrier wax;
 (d) 20 to 50% w/w of film former; and
 (e) 2 to 8% w/w of plasticizer.

In another embodiment of the invention, the wafer comprises of:
 (a) 25 to 35% w/w of fenofibrate;
 (b) 20 to 30% w/w of surfactant;
 (c) 4 to 10% w/w of carrier wax;
 (d) 30 to 40% w/w of film former; and
 (e) 3 to 6% w/w of plasticizer.

In another embodiment of this aspect of the invention, the above embodiments do not contain any super disintegrant.

In another embodiment of the invention, the wafer additionally contains an amount of super disintegrant in a range selected from the group consisting of 2 to 40% w/w; 25 to 35% w/w; 10 to 20% w/w and 2 to 10% w/w.

Another aspect of the invention is a capsule which encapsulates a composition which of fenofibrate, surfactant, carrier wax, film former, plasticizer, super disintegrant and optionally additional ingredients.

In one embodiment of the invention, the composition encapsulated by the capsule comprises of:
 (a) 10 to 50% w/w of fenofibrate;
 (b) 10 to 50% w/w of surfactant;
 (c) 1 to 30% w/w of carrier wax;
 (d) 2 to 40% w/w of film former;
 (e) 1 to 10% w/w of plasticizer; and
 (f) 2 to 40% w/w of super disintegrant.

In another embodiment of the invention, the composition encapsulated by the capsule comprises of:
 (a) 20 to 40% w/w of fenofibrate;
 (b) 15 to 45% w/w of surfactant;
 (c) 2 to 20% w/w of carrier wax;
 (d) 15 to 35% w/w of film former;
 (e) 2 to 8% w/w of plasticizer; and
 (f) 10 to 20% w/w of super disintegrant.

In another embodiment of the invention, the composition encapsulated by the capsule comprises of:
 (a) 25 to 35% w/w of fenofibrate;
 (b) 20 to 30% w/w of surfactant;
 (c) 4 to 10% w/w of carrier wax;
 (d) 15 to 35% w/w of film former;
 (e) 3 to 6% w/w of plasticizer; and
 (f) 10 to 20% w/w of super disintegrant.

In another embodiment of the invention, when the amount of film former is 2 to 10% w/w, the amount of super disintegrant is 25 to 35% w/w. In another embodiment of the invention, when the amount of film former is 15 to 25% w/w, the amount of super disintegrant is 10 to 20% w/w. In another embodiment of the invention, when the amount of film former is 25 to 35% w/w, the amount of super disintegrant is 2 to 10% w/w.

In another embodiment of the invention, the composition encapsulated by the capsule is in the form of fine particles with size ranges selected from the group of of 40 µm-400 µm, 40 µm-200 µm, 50 µm-100 µm, 5 µm-100 µm, 5 µm-50 µm, and 10 µm-25 µm in diameter.

In another embodiment of this invention, the fenofibrate has a solubility in water (at room temperature (20-25° C.) and physiological pH) selected from the ranges of less than 0.20 mg/mL; less than 0.10 mg/mL; and less than 0.05 mg/mL.

In another embodiment of the invention, the wafer or capsule has a residual moisture selected from the ranges of less than 10% by weight, less than 5% by weight; and less than 1% by weight (all weights based on the total weight of the wafer or capsule).

In one embodiment of the invention, the surfactants include, but are not limited to those surfactants used in mucoadhesive films such as those described in U.S. Pat. Nos. 5,948,430; 6,284,264; 6,592,887 and 6,709,671 (assigned to LTS LohmannTherapie-Systeme AG) and may be one or more cationic surfactants, anionic surfactants, non-ionic surfactants. Combination of surfactants can include embodiments wherein the first component may be a polyoxyethylene sorbitan fatty acid ester or a α-hydro-Ω-hydroxypoly (oxyethylene)poly(oxypropylene)poly(oxyethylene) block copolymer, while the second component may be a polyoxyethylene alkyl ether or a polyoxyethylene castor oil derivative. One embodiment of the surfactant is that the HLB value of the polyoxyethylene sorbitan fatty acid ester is between 10 and 20, e.g. a range of 13 to 17. The α-hydro-Ω-hydroxypoly(oxyethylene)poly(oxypropylene) poly(oxyethylene) block copolymer can contain at least 35 oxypropylene-units, e.g. not less than 50 oxypropylene-units.

Alternatively, other surfactants, include, but are not limited to, lecithin, cetyl alcohol, sodium lauryl sulfate, the Spans™ and Tweens™ which are commercially available from ICI Americas, Inc. Ethoxylated oils, including ethoxylated castor oils, such as Cremophor® which is commercially available from BASF, are also useful. Carbowax™ is yet another modifier which is very useful in the present invention. Tween™. or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

In one embodiment of the invention, the surfactants are selected from the group consisting of PEG 8000, PEG 400, mono-, di- and tri-glycerides of behenic acid, polyoxyl 40 hydrogenated castor oil, polyoxyethylene (80) sorbitan monooleate and mixtures thereof.

In one embodiment of this aspect of the invention, the carrier wax material includes, but is not limited to animal waxes, vegetable waxes, mineral waxes, petroleum waxes and synthetic waxes.

Animal waxes include but are not limited to beeswax, spermaceti (main constituent cetyl palmitate) and lanolin. Vegetable waxes include but are not limited to carnuba wax, candelilla wax, ouricury wax, sugarcane wax, retamo wax, jojoba oil, and epicuticular waxes. Petroleum waxes include paraffins, microcrystalline wax, petroleum jelly, montan wax and mixtures of saturated alkanes. Synthetic waxes include but are not limited to waxes from the cracking of polyethylenes, Fischer-Tropsch waxes, substituted amide waxes and polymerized α-olefins.

In one embodiment of the invention, the carrier wax is sorbitan stearate.

In one embodiment of this aspect of the invention, the film forming polymers include, but are not limited to cellulose and cellulose derivatives, such as, methyl cellulose, ethyl cellulose, hydroxyethyl cellulose, hydroxypropyl cellulose, hydroxypropylmethyl cellulose, carboxymethyl cellulose, sodium carboxymethyl cellulose, synthetic or natural gums, such as, xanthan gum, tragacanth gum, guar gum, acacia gum, arabic gum, locust bean gum, methacrylic acid polymers, methacrylic acid copolymers, acrylic acid polymers, acrylic acid copolymers, polyacrylamides, polyalkylene oxides, polyalkylene glycols, pullulan, bean starches, pea starches, polyvinyl pyrrolidone, polyvinyl alcohol, carrageenan, alginic acid, salts of alginic acid, carboxyvinyl polymers, pectin, pectin derivatives, xanthan gum, xanthan gum derivatives, starch and starch derivatives and mixtures thereof.

In another embodiment of the invention, the film forming polymer is hydroxypropylmethyl cellulose, methyl cellulose, sodium carboxymethylcellulose, sodium alginate and mixtures thereof.

In one embodiment of the invention, the plasticizers include, but are not limited to adipates, benzoates, 1,2-propanediol and/or 1,3- and/or 1,4-butanediol and/or polypropylene glycol polyesters with adipic acid, acetic acid or $C_{10}$-$C_{18}$ fatty acids or n-octanol and/or n-decanol, trimellitates, phosphates, sebacates, alkyl sulphonates, epoxidized linseed and soybean oils, DINCH® and/or citrates, alkylene glycols, polyalkylene glycols, glycerol (glycerin), triacetin, deacetylated monoglyceride, polyethylene glycols, diethyl salate, triethyl citrate and mixtures thereof.

The term "super disintegrants" is a term of art which refers to the substances which can be used as disintegrants at lower levels than starch, a widely used disintegrant in tablets. Augsburger et al., "Super Disintegrants: Characterization and Function" from *Encyclopedia of Pharmaceutical Technology*, Third Edition, Volume 6, ed. by James Swarbrick, pages 3553-3567 (2008). Examples of superdisintegrants include, but are not limited to modified starches such as sodium carboxymethyl starch, sodium starch glycolate; cross-linked polyvinylpyrrolidones such as crospovidone; modified celluloses such as internally cross-linked sodium carboxymethylcellulose, e.g. croscarmellose; and chitosans of various molecular weights.

In another embodiment of the invention, the super disintegrant is chitosan.

In another embodiment of the invention, the average molecular weight range of chitosan is selected from the ranges consisting of from 25 kD to 10,000 kD, 500 kD to 5,000 kD, 100 kD to 2,000 kD and 50 kD to 1,000 kD. (Weight-average molecular weight as determined by gel permeation chromatography (GPC)/size exclusion chromatography (SEC))

In another embodiment of this aspect of the invention, the wafers and capsules of the invention may optionally contain one or more additional ingredients which include, but are not limited to disintegrants, taste masking agents, flavoring agents, sweeteners, coloring agents, antioxidants, chelating agents, antimicrobial agents, preservatives, mucoadhesives, permeation enhancers and mixtures thereof.

These optional ingredients can be present in an amount from 0 to 10% w/w. In another embodiment of the invention the amount of optional ingredients is 0.1 to 2% w/w. In another embodiment of the invention the amount of optional ingredients is 0.5 to 5% w/w.

In one embodiment of this aspect of the invention, the wafers and capsules further comprise disintegrants which include, but are not limited to bentonite, pectin, silica gel, carbopol, carrageenan, sodium alginate, xanthan gum, gellum gum, guar gum, Aratex hydoxy propyl starch, corn starch, gum Arabic, locust bean gum, tragacanth, PEG with various molecular weights, anionic and cationic ion exchange resins and maltodextrin.

In another embodiment of the invention, the wafers and capsules further comprise an active ingredient used in the film can be coated to mask the taste of the active ingredient or to prevent the active ingredient from numbing the tongue or other surfaces in the oral cavity. The coatings that can be used are known to those skilled in the art. These include polymers such, as Eudragit® E, cellulosics, such as ethylcellulose, and the like.

An additional way to mask the taste of the active ingredient is by using an ion exchange resin such as Amberlite IRP-69, available from Rohm and Haas, and Dow XYS-40010.00, available from the Dow Chemical Co. or by other means known in the art, e.g.

U.S. Pat. No. 7,615,235 describes forming film-shaped or wafer-shaped pharmaceutical preparations which contain at least one active substance and at least one gas-forming component (e.g. a carbon dioxide forming substance) to mask taste.

U.S. Pat. No. 5,593,684 describes the use of terpene-containing plant secretions as "ethereal oils" in lozenges for oral application in order to mask the unpleasant taste of nicotine.

In another embodiment of the invention, the wafers and capsules further comprise flavoring agents which include, but are not limited to essential oils or extracts of menthol, wintergreen, peppermint, sweet mint, spearmint, vanillin, cherry, butterscotch, chocolate, cinnamon, clove, lemon, orange, raspberry, rose, spice, violet, herbal, fruit, strawberry, grape, pineapple, vanilla, peppermint, peach, kiwi, *papaya*, mango, coconut, apple, coffee, plum, watermelon, nuts, green tea, grapefruit, banana, butter, and chamomile.

In another embodiment of the invention, the wafers and capsules further comprise sweeteners which include, but are not limited to dextrose, lactose, fructose, mannitol, sucrose, trehalose, sucralose, xylitol, mannitol, aspartame, saccharin, sorbitol, sodium saccharin, sodium cyclamate, acesulfame, honey, isomalt, maltodextrin, dextrin, dextrates and mixtures thereof.

In another embodiment of the invention, the wafers and capsules further comprise coloring agents which include, but are not limited to edible pigments, dyes, natural food colors, and synthetic colorants such as FD&C coloring agents and mixtures thereof.

In another embodiment of the invention, the wafers and capsules further comprise antioxidants which include, but are not limited to chelating agents, sodium bisulfite, sodium metabisulfite, ascorbic acid, ascorbyl palmitate.

In another embodiment of the invention, the wafers and capsules further comprise chelating agents which include, but are not limited to EDTA and EGTA.

In another embodiment of the invention, the wafers and capsules further comprise antimicrobial agents and preservatives which include, but are not limited to butylated hydroxyanisol, butylated hydroxyltoluene, parabens, parebens derivatives, sorbic acids and derivatives, benzoic acid and derivatives, propionic acid and derivatives, acetic acid and derivatives and mixtures thereof.

In another embodiment of the invention, the wafers and capsules further comprise mucoadhesives which include, but are not limited to edible silicone, polyacrylic acids, Carbopols®, etc.

In another embodiment of the invention, the permeation enhancers include, but are not limited to non-ionic surfactants, such as poloxamer, Brij®, Span®, Myrj®, Tween®, bile salts, sodium glycodeoxycholate, sodium glycocholate, sodium taurodeoxycholate, sodium taurocholate, Ozone®, fatty acids, such as oleic and caprylic acid derivatives, cyclodextrins, such as α-, β-, γ-cyclodextrin, methylated β-cyclodextrins, chelators, such as EDTA, sodium citrate and polyacrylates; and cationic amino acids, such as poly-L-arginine, L-lysine.

Other excipients and pharmaceutically acceptable agents can also be added such as those described in Remington—The Science and Practice of Pharmacy, $21^{st}$ Edition (2005), Goodman & Gilman's The Pharmacological Basis of Therapeutics, $11^{th}$ Edition (2005) and Ansel's Pharmaceutical Dosage Forms and Drug Delivery Systems ($8^{th}$ Edition), edited by Allen et al., Lippincott Williams & Wilkins, (2005).

Another aspect of the invention is directed toward the process of making a wafer with a dosage of a fenofibrate which comprises:
  (a) forming a hot melt with a fenofibrate, an emulsifier and a carrier wax material;
  (b) homogenizing the hot melt and adding the hot melt to an aqueous solution to form an oil-in-water (O/W) emulsion with microparticles of the BCS class II compound;
  (c) cooling the O/W emulsion and adding a film forming polymer and optionally, a super disintegrant, to form a liquid mass; and
  (d) drying the liquid mass to form a film; and
  (e) cutting the film to form the wafer.

Another aspect of the invention is directed toward the process of making a capsule with a dosage of fenofibrate which comprises:
  (a) forming a hot melt with fenofibrate, an emulsifier and a carrier wax material;
  (b) homogenizing the hot melt and adding the hot melt to an aqueous solution to form an oil-in-water (O/W) emulsion with microparticles of fenofibrate;
  (c) cooling the O/W emulsion and adding a film forming polymer and optionally, a super disintegrant, to form a liquid mass; and
  (d) drying the liquid mass to form a film;
  (e) cutting the film to form the wafer;
  (f) forming the fine particles from the wafer;
  (g) mixing the fine particles with a super disintegrant to form a particle mixture; and
  (h) loading the particle mixture into a capsule.

In another embodiment of the invention, the forming of the fine particles can be accomplished by using a razor to produce particles with a size ranges of 40 μm-400 μm, 40 μm-200 μm, and 50 μm-100 μm in diameter.

In another embodiment of the invention, the forming of the fine particles can be accomplished by freeze milling to produce particles with a size ranges of 5 μm-100 μm, 5 μm-50 μm, and 10 μm-25 μm in diameter.

Another aspect of the invention is a method of lowering cholesterol and/or triglyceride levels to by administering to a patient in need thereof the wafer or capsule of the invention.

In one embodiment of the invention, the administration is via oral, buccal, sublingual, or transmucosal administration.

In another embodiment of the invention, the active agent is released at a rate selected from the rates consisting of at least 75% by weight within 60 minutes of administration; at least 85% within 60 minutes of administration; and at least 90% within 60 minutes of administration (% by weight based on the total weight of the active present).

In another embodiment of the invention, the active agent is released at a rate selected from the rates consisting of at least 75% by weight within 45 minutes of administration; at least 85% within 45 minutes of administration; and at least 90% within 45 minutes of administration (% by weight based on the total weight of the active present).

In another embodiment of the invention, the active agent is released at a rate selected from the rates consisting of at least 75% by weight within 30 minutes of administration; at least 85% within 30 minutes of administration; and at least 90% within 30 minutes of administration (% by weight based on the total weight of the active present).

The invention is further described by the following non-limiting examples which further illustrate the invention, and are not intended, nor should they be interpreted to, limit the scope of the invention.

Operative Examples

The subject matter of the present invention is elucidated in more detail below, using examples, without any intention that the subject matter of the invention should be confined to these exemplary embodiments.

Formation of Wafers and Capsules
I. Hot Melt Formation
Fenofibrate
Compitrol® 888 (mono-, di- and triglycerides of behenic acid)
Sorbitan stearate
Cremophor® RH40 (polyoxyl 40 hydrogenated castor oil)

Fenofibrate is heated together with Compitrol® 888, sorbitan stearate and Cremphor® RH40 in a small beaker up to 100° C. until dissolved. The hot melt mixture is stirred with a spatula until uniform if necessary.

II. Formation of Emulsion with Microparticles of Fenofibrate
Hot melt mixture
Purified water
Polysorbate 80 (polyoxyethylene (80) sorbitan monooleate)

Purified water and polysorbate 80 is heated to 100° C. on a hot plate. Homogenize and stir the mixture at 21,500 rpm (adjust speed to avoid splashing). Gradually add the hot melt and continue the homogenization to form an oil-in-water (O/W) emulsion with microparticles of fenofibrate. While homogenizing, remove hot plate (heat). Stop homogenization and mix at 1,000 rpm. Add crushed ice cubes at the rate of one teaspoon per second and record final temperature of the emulsion with microparticles of fenofibrate. Use ice bath to maintain temperature at 15° C.

III. Formation of Wafers
Emulsion with microparticles of fenofibrate
Sodium CMC (Carboxymethylcellulose)
Chitopharm® M (Chitosan)—optional
Cremophor® RH 40
Glycerin To the emulsion with microparticles of fenofibrate, while mixing at 400 rpm, add sodium CMC (Cekol® 30P) and optionally, gradually add chitosan (Chitopharm® M). Increase mixing speed to 800 rpm for 60 minutes. Add Cremphor® RH 40 and glycerin and continue mixing at 800 rpm for 15 minutes to form a liquid mass.

Cast the liquid mass onto an intermediate liner (process liner) using a 1000 μm wet gap, with the manual coater available in the laboratory. The liquid mass was oven dried at 35° C. for 15-20 minutes, resulting in a dry film.

Wafers were cut into defined sizes out of the resulting dry film with a suitable die-cutter. The cut wafers were then separated from the film and inserted into prefabricated pouches.

Examples of Wafers

TABLE 1

(without super disintegrant)

| Compound | % w/w | | | | |
|---|---|---|---|---|---|
| | Ex. 1 | Ex. 2 | Ex. 3 | Ex. 4 | Ex. 5 |
| Fenofibrate | 35.0 | 27.8 | 33.0 | 30.0 | 30.0 |
| PEG 8000 | 22.0 | | | | |
| PEG 400 | 3.0 | | | | |
| Compitrol ® 888 | | 18.5 | 12.0 | 10.0 | 10.0 |
| Polysorbate ® 80 | | 2.8 | 3.0 | 5.0 | 5.0 |
| Cremophor ®RH40 | | 4.6 | 7.0 | 10.0 | 11.0 |
| Sorbitan stearate (wax) | | 9.3 | 5.0 | 5.0 | 6.0 |
| Metolose ® 60SH50 (hydroxypropylmethyl cellulose/methylcellulose) | 5.0 | 4.6 | 5.0 | 5.0 | 5.0 |
| Pharmacoat ® 603 (hydroxypropylmethylcellulose) | 29.0 | | | | |
| Cekol ® 30P (sodium carboxymethylcellulose) | | 27.6 | 30.0 | 30.0 | 30.0 |
| Glycerin | 6.0 | 4.6 | 5.0 | 5.0 | 3.0 |

TABLE 2

(with super disintegrant)

| Compound | % w/w | | | | | |
|---|---|---|---|---|---|---|
| | Ex. 6 | Ex. 7 | Ex. 8 | Ex. 9 | Ex. 10 | Ex. 11 |
| Fenofibrate | 30.0 | 30.0 | 30.0 | 30.0 | 30.0 | 30.0 |
| Compitrol ® 888 | 10.0 | 10.0 | 10.0 | 10.0 | 10.0 | 10.0 |
| Polysorbate ® 80 | 5.0 | 5.0 | 5.0 | 5.0 | 5.0 | 5.0 |
| Cremophor ®RH40 | 10.0 | 10.0 | 10.0 | 10.0 | 10.0 | 10.0 |
| Sorbitan stearate (wax) | 5.0 | 5.0 | 5.0 | 5.0 | 5.0 | 5.0 |
| Metolose ® 60SH50 (hydroxypropylmethyl cellulose/methylcellulose) | 5.0 | | | | | |

TABLE 2-continued (with super disintegrant)

| Compound | % w/w | | | | | |
|---|---|---|---|---|---|---|
| | Ex. 6 | Ex. 7 | Ex. 8 | Ex. 9 | Ex. 10 | Ex. 11 |
| Cekol ® 30P (sodium carboxymethylcellulose) | | 20.0 | 20.0 | 30.0 | | |
| Manucol ® LD (sodium alginate) | | | | | 30.0 | 20.0 |
| Glycerin | 5.0 | 5.0 | 5.0 | 5.0 | 5.0 | 5.0 |
| Sodium starch glycolate | 30.0 | 15.0 | | | | |
| Chitopharm ® M (milled or non-milled) | | | 15.0 | | | 15.0 |
| Chitopharm ® M (milled) | | | | 5.0 | 5.0 | |

Figure 2:
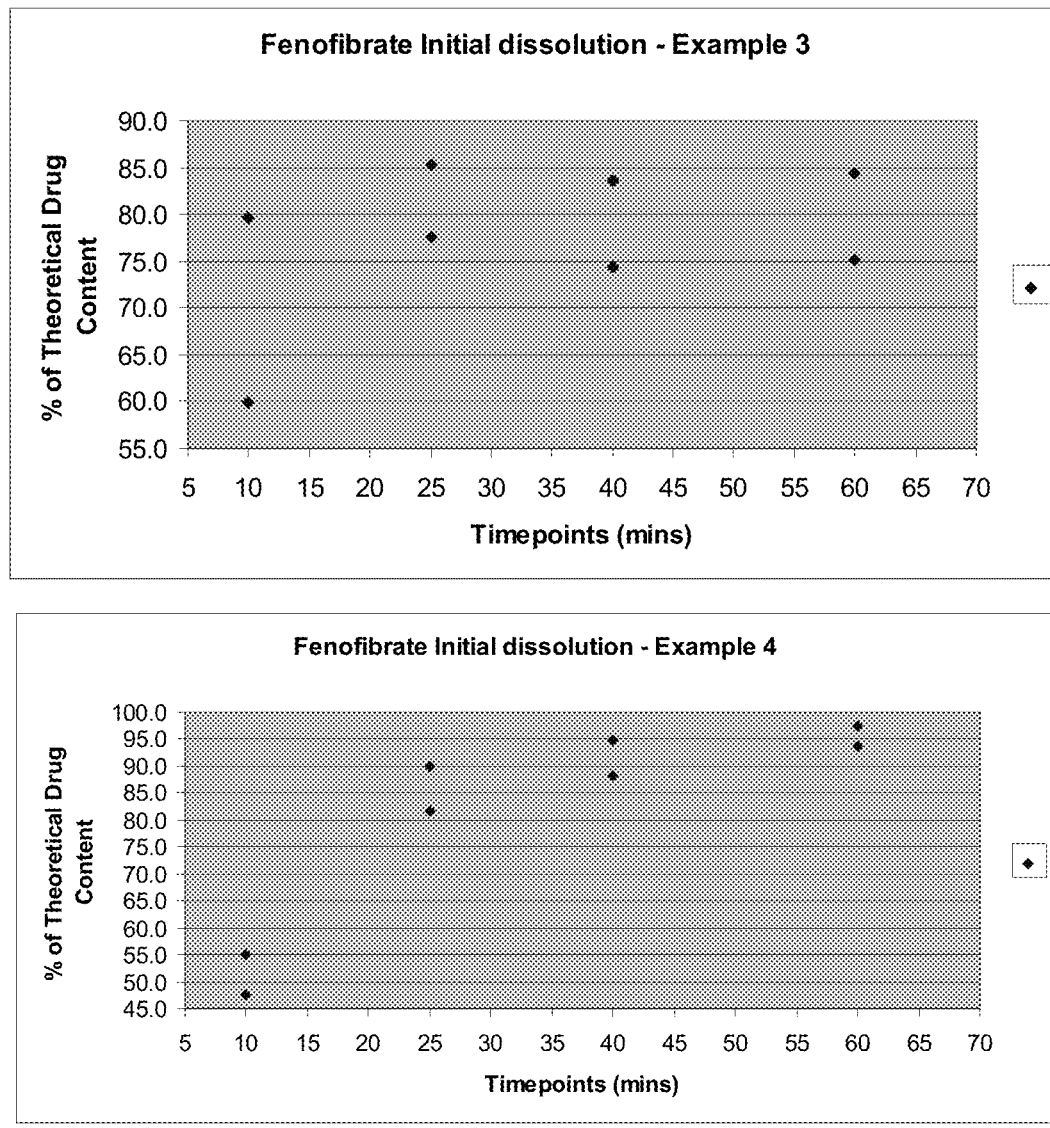
FIG. 2 depicts the wafer dissolution rate of Examples 3 and 4.
Figure 3:
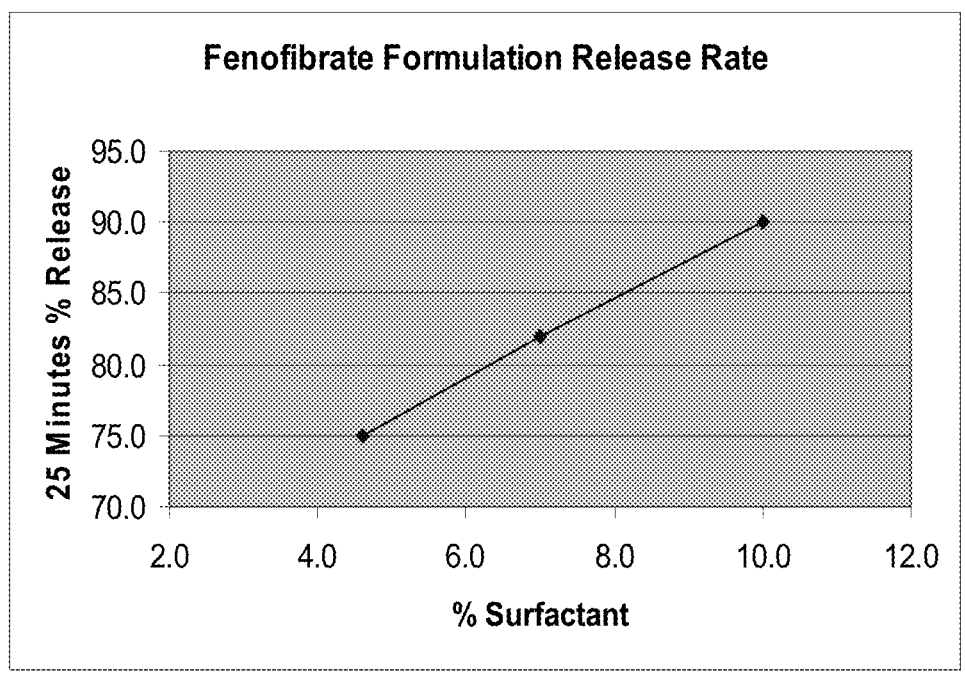
FIG. 3 depicts the control of release rate by adjusting Cremophor RH 40 concentration

The wafer dissolution rate are shown in FIG. 1 (for example 2) and FIG. 2 (for examples 3 and 4). The release rate of fenofibrate was controlled by adjusting Cremophor® RH 40 concentration and is depicted in FIG. 3 which shows a linear relationship between the amount of surfactant and the % release of fenofibrate.

IV. Formation of Capsules

The wafers were cut using a doctor's knife or razor to a particle size between 40 μm-400 μm in width. The particles were filled into 150 mg and 450 mg capsules, corresponding to fenofibrate content approximately 50 mg (low dose) and 150 mg (high dose), respectively. The capsules were then subjected to USP dissolution using triplicate samples.

V. Capsule Dissolution Rate without Super Disintegrants

Figure 4:
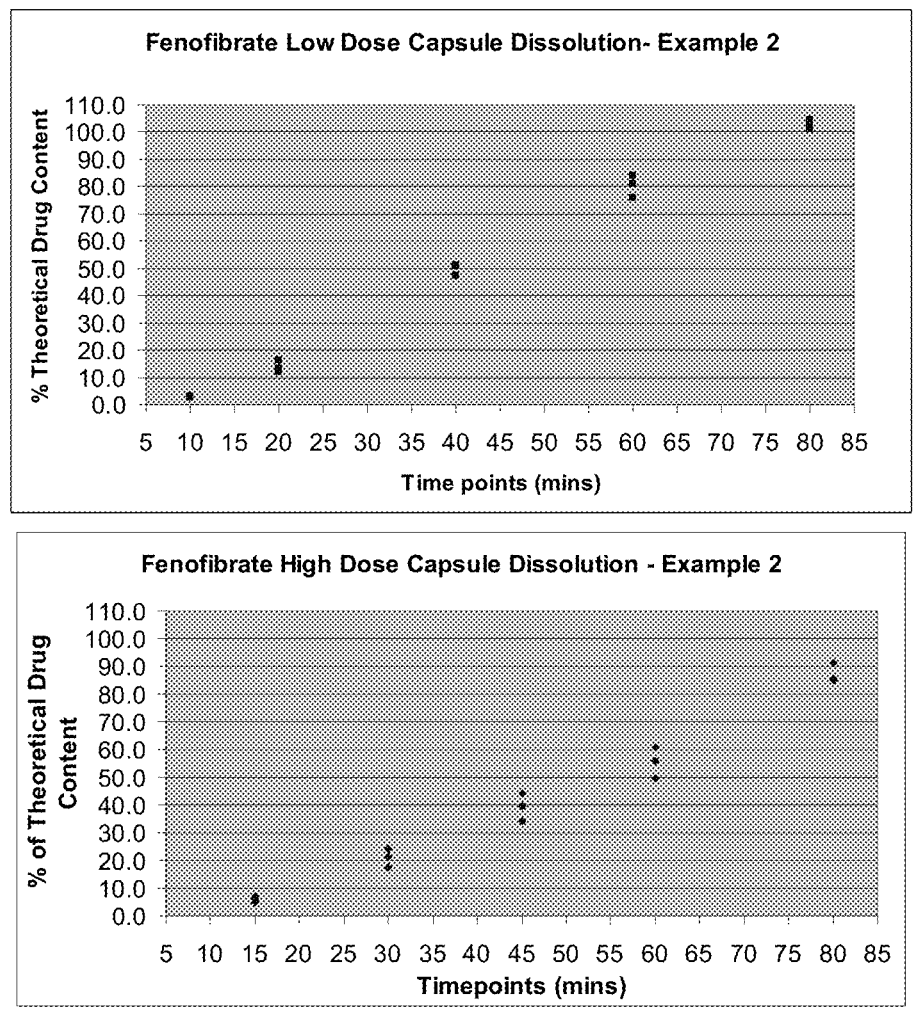
FIG. 4 depicts the capsule formulation dissolution rate without super disintegrants for Example 2 (low dose and high dose capsules)
Figure 5:
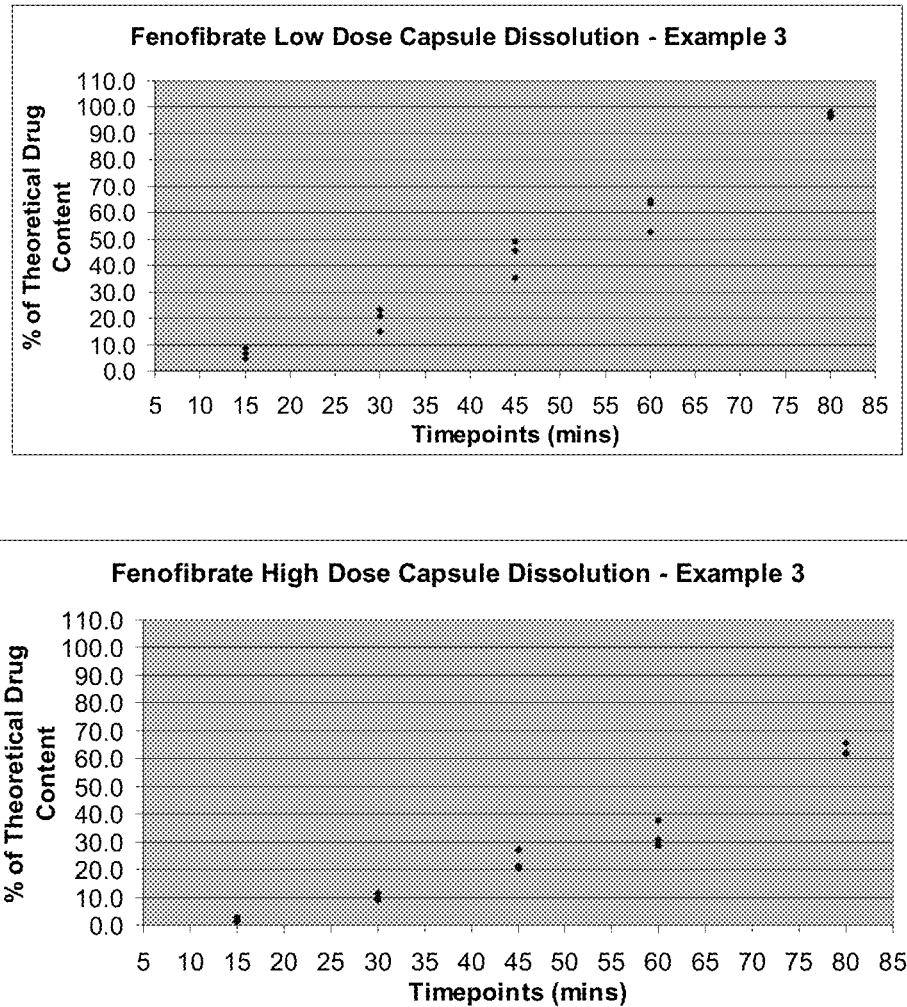
FIG. 5 depicts the capsule formulation dissolution rate without super disintegrants for Example 3 (low dose and high dose capsules)
Figure 6:
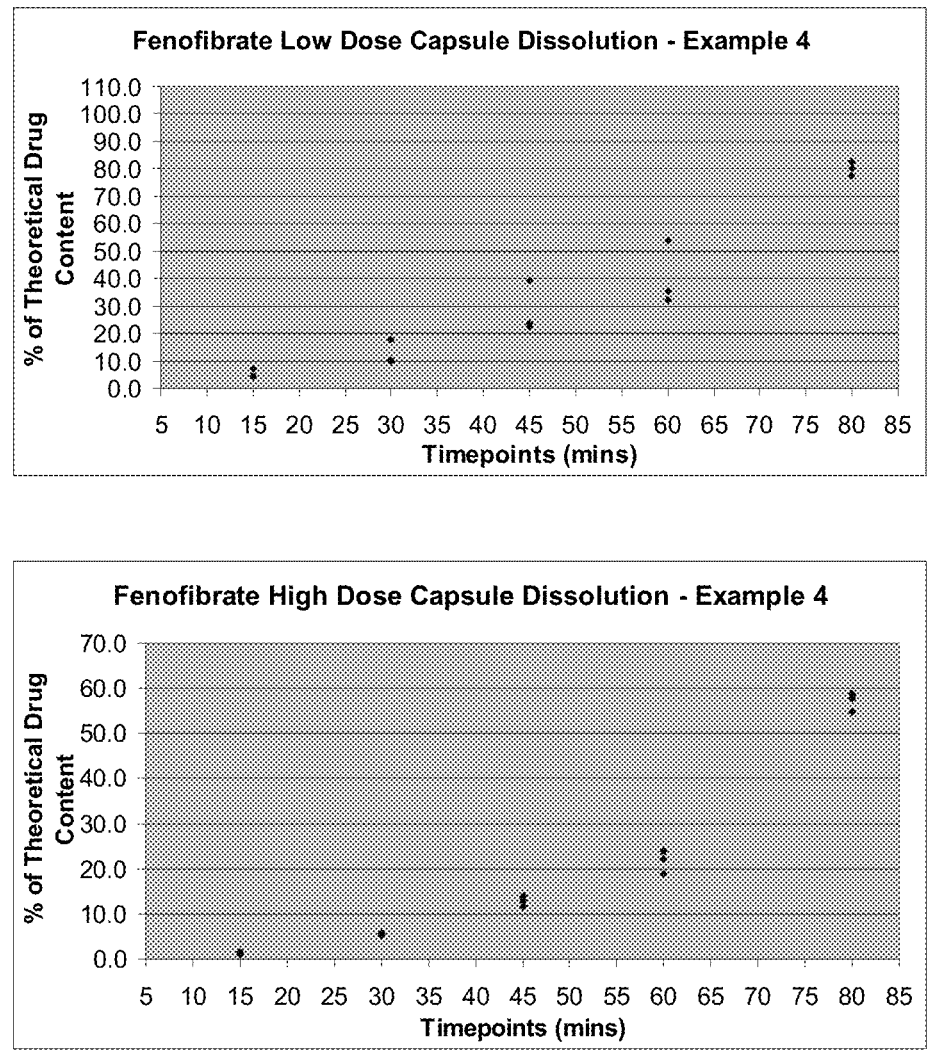
FIG. 6 depicts the capsule formulation dissolution rate without super disintegrants for Example 4 (low dose and high dose capsules)
Figure 8:
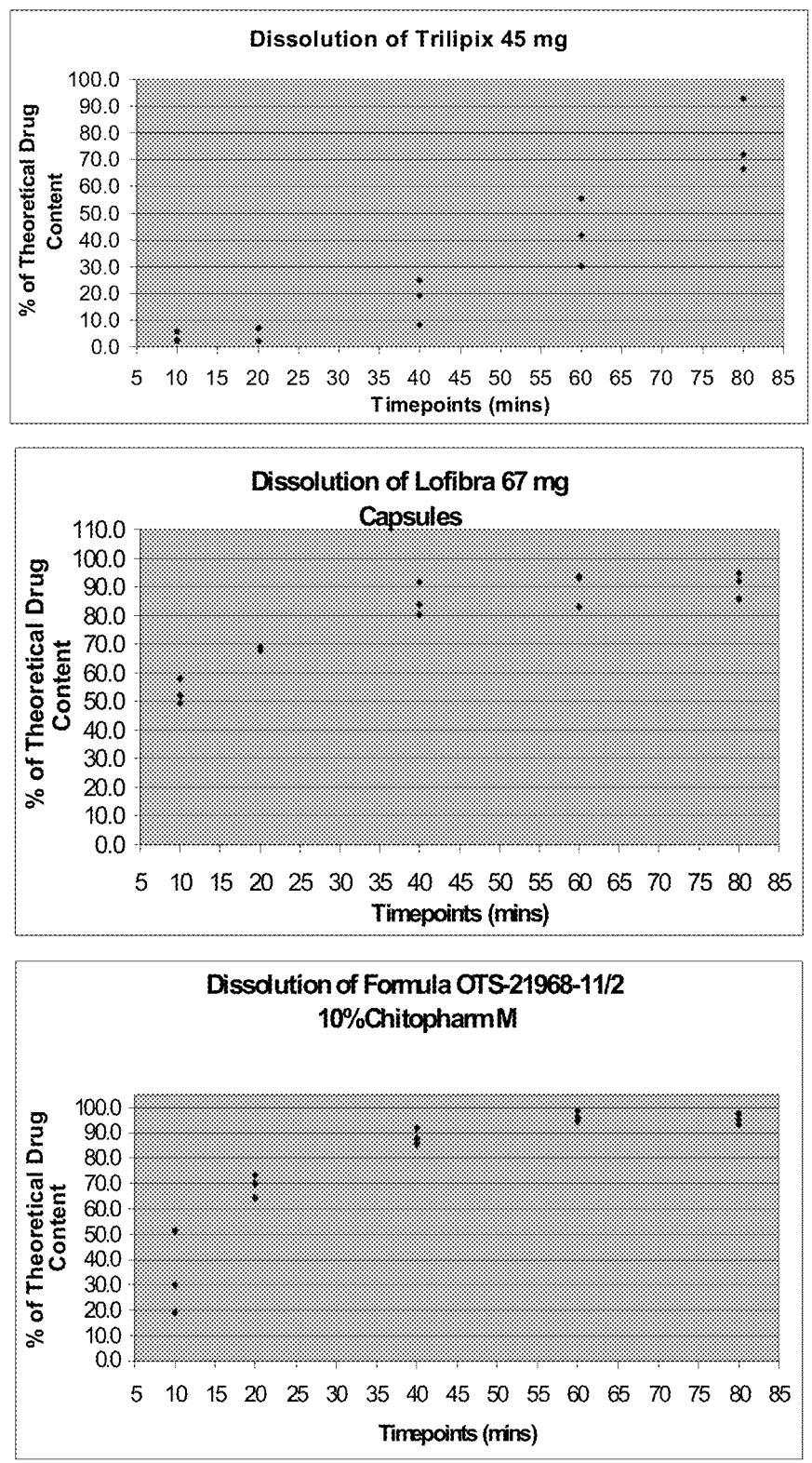
FIG. 8 depicts the comparison of various low dose dissolution rates (top—Abbott Laboratories low dose Trilipix (fenofibrate); middle—Teva Pharmaceuticals low dose Lofibra® (fenofibrate); bottom—LTS Lohmann low dose fenofibrate (10% Chitopharm M, disclosed in Table 3) not commercially available FIG. 9 depicts the comparison of various high dose dissolution rates (top—Abbott Laboratories high dose Trilipix (fenofibrate); middle—Teva Pharmaceuticals high dose Lofibra® (fenofibrate); bottom—LTS Lohmann high dose fenofibrate (10% Chitopharm M, disclosed in Table 4) not commercially available
Figure 9:
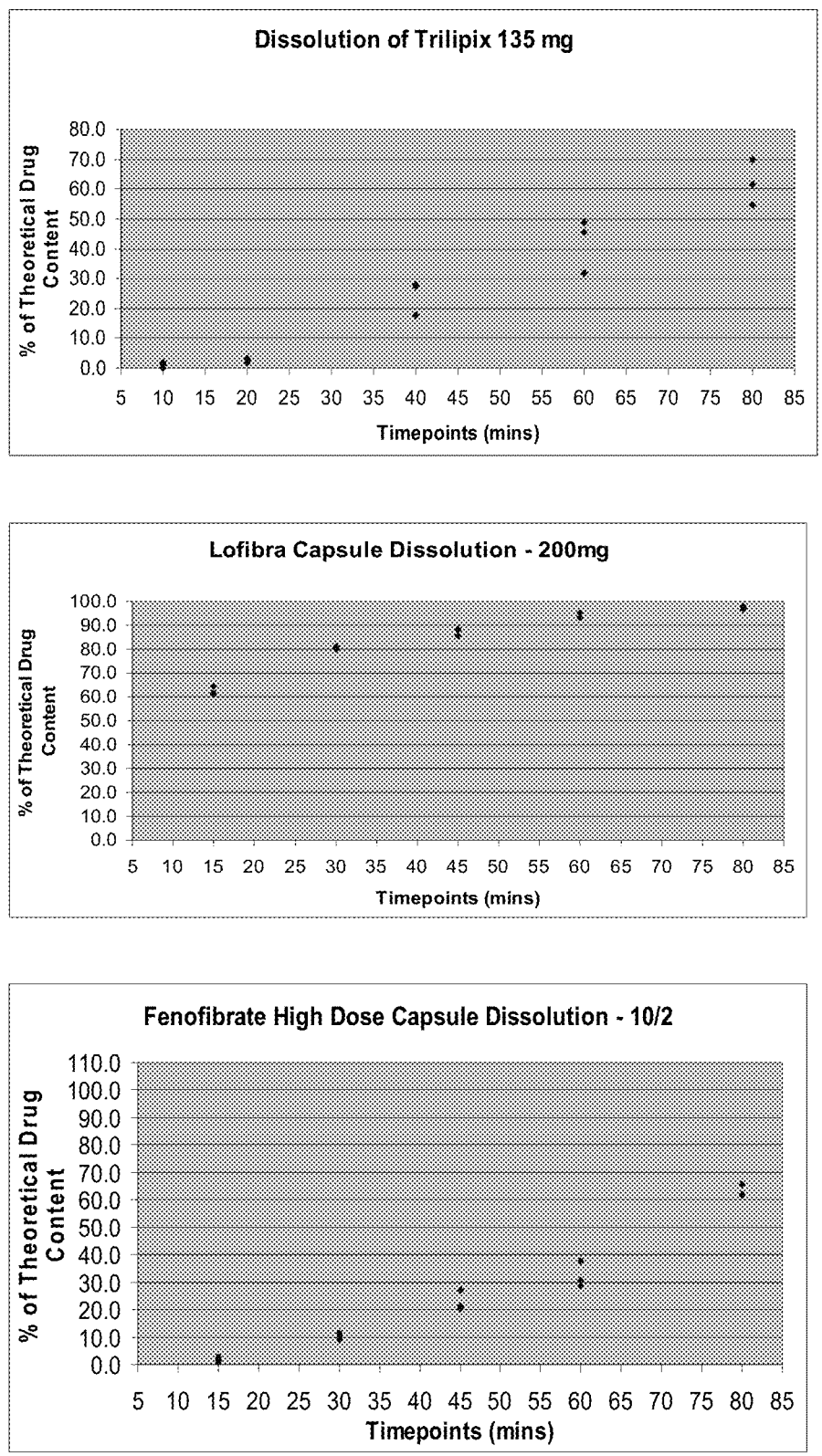

The capsule dissolution rates without super disintegrants are shown in FIGS. 4, 5 and 6. As can be seen from these figures, the % w/w of fenofibrate released is linear with respect to time.

VI. Capsule Dissolution Rate with Super Disintegrants

The capsule dissolution rate with super disintegrants (Chitopharm®—Chitosan) are shown in FIG. 7. As can be seen from FIG. 7, the % w/w of fenofibrate released is hyperbolic with respect to time. 60% of fenofibrate release was achieved at 20 minutes for 6.3% chitosan and 70% of fenofibrate release was achieved for 10% chitosan.

VII. Comparative Screening Studies (Super Disintegrant Screening Vs. Disintegrants)

Super disintegrants, such as, croscarmellose (crosslinked sodium carboxymethylcellulose), sodium starch glycolate, crospovidone (polyvinylpyrrolidone), in addition to Chitopharm® L, M and S (chitosan) were studied using a dissolution screening method and compared against the use of disintegrants such as effervescent technology, bentonite, pectin, Carbopol® (polymers of acrylic acid cross-linked with polyalkenyl ethers or divinyl glycol), carrageenan, sodium alginate, xanthum gum, gellum gum, tragacanth. The same dissolution bath, dissolution media and sinker were used. The dissolution time of capsules were observed.

Super Disintegrant and Disintegrant Screening Results

TABLE 3

Various Polymers for Low Dose Fenofibrate (167 mg capsule Weight)

| Formulation (Ex. #) | Polymer Added | 10 min | 20 min | 30 min | 40 min | 50 min | Comments |
|---|---|---|---|---|---|---|---|
| 5 | Kollidon CL 3% | 0% | 20% | 40% | 60% | 100% | Particle Floating |
| 5 | Croscarmellose 5% | 0% | 25% | 40% | 50% | 60% | 70% out at 60 min |
| 5 | Bentonite 5% | 0% | 0% | 10% | 30% | 70% | 100% out at 60 min |
| 5 | Bentonite 5% and Crospovidone 5% | 5% | 10% | 25% | 35% | 45% | 100% out at 60 min |
| 5 | 2.5% pectin and 2.5% Silica gel | 0% | 15% | 20% | 50% | 100% | Particle Floating |
| 5 | Carbopol 971 5% | 5% | 10% | 15% | 25% | 50% | 60% out at 60 min |
| 5 | Carrageenan 5% | 0% | 20% | 50% | 60% | 75% | 100% out at 60 min |
| 5 | Sodium alginate 5% | 5% | 10% | 15% | 20% | 40% | 60% at 60 min |
| 5 | Xanthan gum 5% | 10% | 15% | 20% | 25% | 60% | 100% out at 60 min |
| 5 | Gellum gum 5% | 5% | 10% | 15% | 20% | 95% | 100% out at 60 min |
| 5 | Tragacanth 5% | 0% | 0% | 40% | 50% | 60% | 70% out at 60 min |
| 5 | Chitopharm ® L 10% | 50% | 80% | 100% | 100% | 100% | 100% out at 30 min |
| 5 | Chitopharm ® M 10% | 30% | 95% | 100% | 100% | 100% | 95% out at 20 min |
| 5 | Chitopharm ® S 10% | 40% | 95% | 100% | 100% | 100% | 95% out at 20 min |
| 5 | Chitopharm ® M 7% and Kollidon ® CL 3% | 50% | 70% | 100% | 100% | 100% | 100% out at 26 min |
| 7 | Chitopharm ® M 10% | 40% | 60% | 65% | 100% | 100% | 100% out at 40 min |
| 7 | Kollidon ® CL 10% | 10% | 50% | 60% | 100% | 100% | 100% out at 40 min |
| 8 | Chitopharm ® M 10% | 75% | 95% | 100% | 100% | 100% | 100% out at 25 min |
| 8 | Kollidon ® CL 10% | 10% | 30% | 50% | 90% | 100% | 100% out at 47 min |
| 9 | Chitopharm M 10% | 40% | 80% | 100% | 100% | 100% | 100% out at 27 min |
| 9 | Kollidon ® CL 10% | 25% | 50% | 60% | 70% | 100% | 100% out at 45 min |
| 10 | (Manucol LD & milled Chitopharm ® M embedded) Chitopharm ® M 10% | 80% | 98% | 99% | 100% | 100% | 100% out at 33 min |
| 10 | (Manucol LD & milled Chitopharm ® M embedded) Kollidon ® CL 10% | 20% | 40% | 50% | 80% | 98% | 100% out at 66 min |
| 11 | (Manucol LD & Chitopharm ® M embedded) Chitopharm ® M 10% | 50% | 70% | 100% | 100% | 100% | 100% out at 23 min |

TABLE 3-continued

Various Polymers for Low Dose Fenofibrate (167 mg capsule Weight)

| Formulation (Ex. #) | Polymer Added | 10 min | 20 min | 30 min | 40 min | 50 min | Comments |
|---|---|---|---|---|---|---|---|
| 11 | (Manucol LD & Chitopharm ® M embedded) Kollidon ® CL 10% | 0% | 35% | 80% | 100% | 100% | 100% out at 36 min |

TABLE 4

Various Polymers for High Dose Fenofibrate (500-550 mg Capsule Weight)

| Formulation (Ex. #) | Polymer Added | 10 min | 20 min | 30 min | 40 min | 50 min | Comments |
|---|---|---|---|---|---|---|---|
| 5 | Chitopharm ® L 10% | 10% | 20% | 30% | 50% | 100% | 100% out at 49 min |
| 5 | Chitopharm ® M 10% | 15% | 25% | 40% | 60% | 100% | 100% out at 47 min |
| 5 | Chitopharm ® S 10% | 15% | 30% | 50% | 70% | 80% | 100% out at 62 min |
| 5 | Chitopharm ® M 7% & Kollidon ® CL 3% | 20% | 40% | 60% | 80% | 85% | 90% out at 60 min |
| 5 | C-Aratex Hydroxypropyl Starch 10% | 0% | 10% | 15% | 20% | 25% | 30% out ay 60 min |
| 5 | Corn Starch 10% | 0% | 15% | 20% | 25% | 30% | 35% Out at 60 min |
| 5 | Gum Arabic 10% | 0% | 5% | 10% | 15% | 20% | 30% out at 60 min |
| 5 | Locust Bean Gum 10% | 5% | 10% | 15% | 20% | 25% | 30% out at 60 min |
| 5 | PEG8000 10% | 0% | 5% | 10% | 15% | 20% | 25% out at 60 min |
| 5 | Amberlite IRP64 10% | 1% | 5% | 10% | 15% | 20% | 25% out at 60 min |
| 5 | Amberlite IRP69 10% | 0% | 1% | 5% | 10% | 15% | 20% out at 60 min |
| 5 | Amberlite IRP88 10% | 0% | 1% | 5% | 10% | 15% | 20% out at 60 min |
| 5 | Maltodextrin 10% | 1% | 2% | 5% | 10% | 15% | 20% out at 60 min |
| 5 | Kollidon ® CL 9.09%, Tartaric Acid 4.55%, Ammonium Bicarbonate 4.55% | 5% | 10% | 15% | 20% | 25% | 40% out at 60 min |
| 7 | Chitopharm ® M 10% | 5% | 10% | 15% | 20% | 30% | 50% out at 70 min |
| 7 | Kollidon ® CL 10% | 0% | 5% | 10% | 15% | 20% | 30% out at 60 min |
| 8 | Chitopharm ® M 10% | 10% | 20% | 35% | 45% | 50% | 65% out at 60 min |
| 8 | Kollidon ® CL 10% | 5% | 10% | 20% | 30% | 35% | 40% Out at 60 min |
| 9 | Chitopharm ® M 10% | 20% | 30% | 40% | 45% | 50% | 60% out at 70 min |
| 9 | Kollidon0 CL 10% | 5% | 10% | 20% | 30% | 35% | 45% Out at 70 min |
| 10 | Chitopharm ® M 10% | 15% | 35% | 41% | 60% | 68% | 100% out at 58 min |
| 10 | Kollidon ® CL 10% | 10% | 20% | 25% | 30% | 35% | 45% out at 70 min |
| 11 | Chitopharm ® M 10% | 20% | 35% | 50% | 75% | 98% | 90% out at 41 min |
| 11 | Kollidon ® CL 10% | 5% | 10% | 30% | 50% | 80% | 85% out at 60 min |

Having thus described in detail various embodiments of the present invention, it is to be understood that the invention defined by the above paragraphs is not to be limited to particular details set forth in the above description as many apparent variations thereof are possible without departing from the spirit or scope of the present invention.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

The invention claimed is:

1. A wafer which is obtained by a process in which an oil-in-water (O/W) emulsion with microparticles of a BSC class II compound is formed, and which comprises a composition comprising:

20 to 40% w/w of fenofibrate;
15 to 45% w/w of a surfactant;
2 to 20% w/w of a carrier wax;
15 to 35% w/w of a film former;
3 to 8% w/w of a plasticizer; and
optionally additional ingredients;
wherein the process comprises
  (a) forming a hot melt with fenofibrate, an emulsifier, a surfactant and a carrier wax material;
  (b) homogenizing the hot melt and adding the hot melt to an aqueous solution to form an oil-in-water (O/W) emulsion with microparticles of fenofibrate;
  (c) cooling the O/W emulsion and adding a film forming polymer, a plasticizer and optionally, a super disintegrant, to form a liquid mass;
  (d) drying the liquid mass at 35° C. for 15 to 20 minutes to form a film; and
  (e) cutting the film to form the wafer.

2. The wafer as claimed in claim 1, further comprising: an amount of super disintegrant in a range of 2 to 40% w/w.

3. The wafer as claimed in claim 2;
wherein the surfactant is selected from the group consisting of one or more cationic surfactants, anionic surfactants, nonionic surfactants, and mixtures thereof;
wherein the carrier wax material is selected from the group consisting of one or more of animal waxes, vegetable waxes, mineral waxes, petroleum waxes, synthetic waxes, beeswax, spermaceti (main constituent cetyl palmitate), lanolin, carnuba wax, candelilla wax, ouricury wax, sugarcane wax, retamo wax, jojoba oil, epicuticular waxes, paraffins, microcrystalline wax, petroleum jelly, montan wax, mixtures of saturated alkanes, waxes from the cracking of polyethylenes, Fischer-Tropsch waxes, substituted amide waxes, polymerized α-olefins, sorbitan stearate, and mixtures thereof;

wherein the film forming polymer is selected from the group consisting of one or more of cellulose, methyl cellulose, ethyl cellulose, hydroxyethyl cellulose, hydroxypropyl cellulose, hydroxypropylmethyl cellulose, carboxymethyl cellulose, sodium carboxymethyl cellulose, synthetic or natural gums, xanthan gum, tragacanth gum, guar gum, acacia gum, arabic gum, locust bean gum, methacrylic acid polymers, methacrylic acid copolymers, acrylic acid polymers, acrylic acid copolymers, polyacrylamides, polyalkylene oxides, polyalkylene glycols, pullulan, bean starches, pea starches, polyvinyl pyrrolidone, polyvinyl alcohol, carrageenan, alginic acid, salts of alginic acid, carboxyvinyl polymers, pectin, xanthan gum, starch, and mixtures thereof;

wherein the plasticizer is selected from the group consisting of one or more of adipates, benzoates, 1,2-propanediol and/or 1,3- and/or 1,4-butanediol and/or polypropylene glycol polyesters with adipic acid, acetic acid or C10-C18 fatty acids or n-octanol and/or n-decanol, trimellitates, phosphates, sebacates, alkyl sulphonates, epoxidized linseed and soybean oils, diisononyl 1,2-cyclohexanedicarboxylic acid and/or citrates, alkylene glycols, polyalkylene glycols, glycerol (glycerin), triacetin, deacetylated monoglyceride, polyethylene glycols, diethyl salate, triethyl citrate, and mixtures thereof; and wherein the super disintegrant is selected from the group consisting of one or more of sodium carboxymethyl starch, sodium starch glycolate, cross-linked polyvinylpyrrolidones, crospovidone, cross-linked sodium carboxymethylcellulose, croscarmellose, chitosan, and mixtures thereof.

4. The wafer as claimed in claim 1, further comprising: a disintegrant.

5. The wafer as claimed in claim 1, further comprising: a taste masking agent that masks the taste of the fenofibrate or that prevents the fenofibrate from numbing a tongue or other surface in an oral cavity.

6. The wafer as claimed in claim 1, further comprising: a flavoring agent.

7. The wafer as claimed in claim 1, further comprising: a sweetener.

8. The wafer as claimed in claim 1, further comprising: a coloring agent.

9. The wafer as claimed in claim 1, further comprising: an antioxidant.

10. The wafer as claimed in claim 1, further comprising: a chelating agent.

11. The wafer as claimed in claim 1, further comprising: an antimicrobial agent and a preservative.

12. The wafer as claimed in claim 1, further comprising: a mucoadhesive.

13. The wafer as claimed in claim 1, further comprising: a permeation enhancer.

14. The wafer as claimed in claim 1, further comprising: at least one substance selected from the group consisting of disintegrants, taste masking agents, flavoring agents, sweeteners, coloring agents, antioxidants, chelating agents, antimicrobial agents, preservatives, mucoadhesives, permeation enhancers, and mixtures thereof.

15. The wafer as claimed in claim 3;

wherein the surfactant is selected from the group consisting of polyoxyethylene sorbitan fatty acid ester, α-hydro-Ω-hydroxypoly (oxyethylene)poly(oxypropylene)poly(oxyethylene) block copolymer, polyoxyethylene alkyl ether, polyoxyethylene castor oils, lecithin, cetyl alcohol, sodium lauryl sulfate, ethoxylated oils, PEG 8000, PEG 400, mono-, di- and tri-glycerides of behenic acid, polyoxyl 40 hydrogenated castor oil, polyoxyethylene (80) sorbitan monooleate, and mixtures thereof.

* * * * *